(12) United States Patent
Boot et al.

(10) Patent No.: US 9,880,318 B2
(45) Date of Patent: Jan. 30, 2018

(54) METHOD FOR ANALYZING CORE SAMPLE FROM WELLBORE, INVOLVES ANALYZING ZONE OF INTEREST IN CORE SAMPLE, AND FORMING IMAGE OF CORE SAMPLE TO SPATIALLY REPRESENT CHARACTERISTICS OF CORE SAMPLE

(71) Applicant: GE Energy Oilfield Technology, Inc., Houston, TX (US)

(72) Inventors: John Boot, Atlanta, GA (US); Ali Can, Niskayuna, NY (US); Thomas Szudajski, Houston, TX (US)

(73) Assignee: GE ENERGY OILFIELD TECHNOLOGY, INC., Houston, TX (US)

( * ) Notice: Subject to any disclaimer, the term of this patent is extended or adjusted under 35 U.S.C. 154(b) by 434 days.

(21) Appl. No.: 14/536,352

(22) Filed: Nov. 7, 2014

(65) Prior Publication Data
US 2016/0131796 A1 May 12, 2016

(51) Int. Cl.
*G01V 8/12* (2006.01)
*G01N 33/24* (2006.01)

(52) U.S. Cl.
CPC .............. *G01V 8/12* (2013.01); *G01N 33/241* (2013.01)

(58) Field of Classification Search
CPC .. G01V 8/12; G01V 5/08; G01T 15/08; G01T 17/00; H04N 13/04; G01N 33/24; G01N 23/046; G01N 2223/649; G01N 2223/419; G01N 21/65; G01N 21/3554; E21B 43/119; E21B 49/00

USPC ....... 345/424; 356/432; 250/255; 73/152.11; 378/54, 56

See application file for complete search history.

(56) References Cited

U.S. PATENT DOCUMENTS

| | | | |
|---|---|---|---|
| 4,583,242 A | 4/1986 | Vinegar et al. | |
| 4,924,187 A | 5/1990 | Sprunt et al. | |
| 5,109,398 A | 4/1992 | Hunt et al. | |
| 5,164,672 A * | 11/1992 | Gilliland | G01N 33/241 |
| | | | 250/255 |
| 5,318,123 A | 6/1994 | Venditto et al. | |
| 5,360,066 A | 11/1994 | Venditto et al. | |
| 6,118,839 A | 9/2000 | Dafni et al. | |
| 6,430,547 B1 | 8/2002 | Busche | |
| 6,816,787 B2 | 11/2004 | Ramamoorthy | |

(Continued)

OTHER PUBLICATIONS

Reddy, B., "An FFT-Based Technique for Translation, Rotation, and Scale-Invariant Image Registration," IEEE Transactions on Image Processing, vol. 5, No. 8, Aug. 1996, pp. 1266-1271.

(Continued)

*Primary Examiner* — Harshad R Patel
*Assistant Examiner* — Brandi Hopkins
(74) *Attorney, Agent, or Firm* — Hogan Lovells US LLP (57) ABSTRACT

A method of analyzing a core sample from a wellbore by creating a visual composite image of the core sample that is based on a scan of the core sample. The scan directs radiation at the core sample, such as a computerized tomography (CT) scan, and obtains scan data by estimating radiation absorbed by material in the core sample. The composite image is made up of an arrangement of voxels, where each voxel represents a designated volume of the core sample, and is are assigned a value that corresponds to a measured value of radiation absorbed in the designated volume of the core sample.

19 Claims, 5 Drawing Sheets

(56) References Cited

U.S. PATENT DOCUMENTS

| | | | |
|---|---|---|---|
| 7,172,038 B2 | 2/2007 | Terry et al. | |
| 7,564,944 B2 | 7/2009 | Kato | |
| 7,714,304 B2 | 5/2010 | Poglitsch | |
| 7,853,045 B2 | 12/2010 | Touati | |
| 8,542,793 B1 | 9/2013 | Jin | |
| 8,590,382 B2 * | 11/2013 | Zaleski, Jr. | E21B 43/119 166/250.01 |
| 2004/0218716 A1 * | 11/2004 | Freifeld | G01N 23/04 378/62 |
| 2010/0324868 A1 * | 12/2010 | Russell | B23K 10/00 703/1 |
| 2012/0230151 A1 | 9/2012 | Almaguer | |
| 2013/0083888 A1 | 4/2013 | Jin | |
| 2014/0086381 A1 | 3/2014 | Grader et al. | |
| 2015/0177409 A1 | 6/2015 | Sofiienko | |
| 2015/0185122 A1 | 7/2015 | Lakshtanov et al. | |
| 2016/0131793 A1 | 5/2016 | Szudajski | |

OTHER PUBLICATIONS

Wang, Qiang et al., "Automatic Registration of Remote Sensing Image with Moderate Resolution," College of Geoscience and Surveying Engineering, CUMT, Beijing, China; Apr. 24-26, 2012; pp. 404-409.

Renard et al., "3D imaging of fracture propagation using synchroton X-ray microtomography," Earth and Planetary Science Letters, 286, 2009, pp. 285-291.

* cited by examiner

METHOD FOR ANALYZING CORE SAMPLE FROM WELLBORE, INVOLVES ANALYZING ZONE OF INTEREST IN CORE SAMPLE, AND FORMING IMAGE OF CORE SAMPLE TO SPATIALLY REPRESENT CHARACTERISTICS OF CORE SAMPLE

BACKGROUND OF THE INVENTION

1. Field of Invention

The present disclosure relates in general to a method and system for analyzing a core sample from a wellbore. More specifically, the present disclosure relates to a method and system for evaluating a core sample from a wellbore with computed tomography.

2. Description of Prior Art

Various techniques are currently in use for identifying the presence of hydrocarbons in subterranean formations. Some techniques employ devices that emit a signal from a seismic source, and receive reflections of the signal on surface. Others involve disposing logging devices downhole in a wellbore intersecting the subterranean formation, and interrogating the formation from within the wellbore. Example downhole exploration devices include seismic tools that can transmit and receive seismic signals, or ones that simply receive a seismic signal generated at surface. Other devices collect and sample fluid from within the formation, or from within the wellbore. Nuclear tools are also employed that direct radiation into the formation, and receive radiation that scatters from the formation. Analyzing the scattered radiation can provide information about fluids residing in the formation adjacent the wellbore, the type of fluid, and information about other materials next to the wellbore, such as gravel pack.

Logging downhole also is sometimes done while the wellbore itself is being drilled. The logging devices are usually either integral with a drill bit used during drilling, or on a drill string that rotates the drill bit. The logging devices typically are either nuclear, seismic, can in some instances optical devices. In some instances, a core is taken from the wellbore and analyzed after being retrieved to the surface. Analyzing the core generally provides information about the porosity and/or permeability of the rock formation adjacent the wellbore. Cores are generally elongated cylindrical members and obtained with a coring tool having an open barrel for receiving and retaining the core sample.

SUMMARY OF THE INVENTION

Disclosed herein is an example of a method of analyzing a core sample by obtaining information about characteristics of the core sample at discrete locations in the core sample, comparing the characteristics with one another, identifying a zone of interest in the core sample based on the step of comparing the characteristics with one another, and analyzing the zone of interest in the core sample. The step of obtaining information about characteristics of the core sample can include scanning the core sample with radiation, monitoring radiation scattered from the core sample, and estimating the amount of radiation absorbed in volumetric spaces of the core sample. The method can further include forming an image of the core sample that spatially represents characteristics of the core sample. In this example, the image has voxels that are strategically located to represent corresponding volumetric spaces of the core sample. Further, the voxels may be assigned a designated value to represent the corresponding characteristics of the volumetric space of the core sample. In an alternative, the designated value is an alpha-numeric attribute. The image can be segments that are coaxially arranged and that represent axial slices of the core sample, and wherein the step of identifying a zone of interest involves identifying changes in characteristics of the core sample represented by multiple segments. In this example, the multiple segments are adjacent one another. The step of comparing the characteristics with one another may include estimating an average value of a one of the characteristics. The zone of interest in the core sample can be identified where there is a change of a characteristic of the material in the core sample. Optionally, the step of analyzing the zone of interest in the core sample includes obtaining a plug from the core sample and scanning the plug with an amount of radiation that exceeds an amount of radiation that scanned the sample plug.

Also disclosed herein is an example of a method of analyzing a core sample that includes measuring a value of radiation absorption at discrete volumetric spaces in the core sample, estimating a physical characteristic of the core sample at each of the discrete volumetric spaces based on the step of measuring the radiation absorption, identifying differences between physical characteristics of proximate discrete volumetric spaces, designating a zone of interest in the core sample to be where the differences between physical characteristics of proximate discrete volumetric spaces exceed a threshold value, and analyzing the zone of interest in the core sample. Voxels may be created that are assigned a location that correlates to the discrete volumetric spaces, and which are assigned a value that represents the physical characteristics of the corresponding discrete volumetric spaces. The method can further include forming a visual image based on the voxels. The method can further include obtaining plugs from the zone of interest. The plugs may be scanned with a computerized tomography scan, or optionally can be analyzed with a spectroscopy. One alternative involves further designating a multiplicity of zones of interest in the core sample and analyzing the zones of interest.

BRIEF DESCRIPTION OF DRAWINGS

Some of the features and benefits of the present invention having been stated, others will become apparent as the description proceeds when taken in conjunction with the accompanying drawings, in which.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The method and system of the present disclosure will now be described more fully hereinafter with reference to the accompanying drawings in which embodiments are shown. The method and system of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout. In an embodiment, usage of the term "about" includes +/−5% of the cited magnitude. In an embodiment, usage of the term "substantially" includes +/−5% of the cited magnitude.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Figure 1:
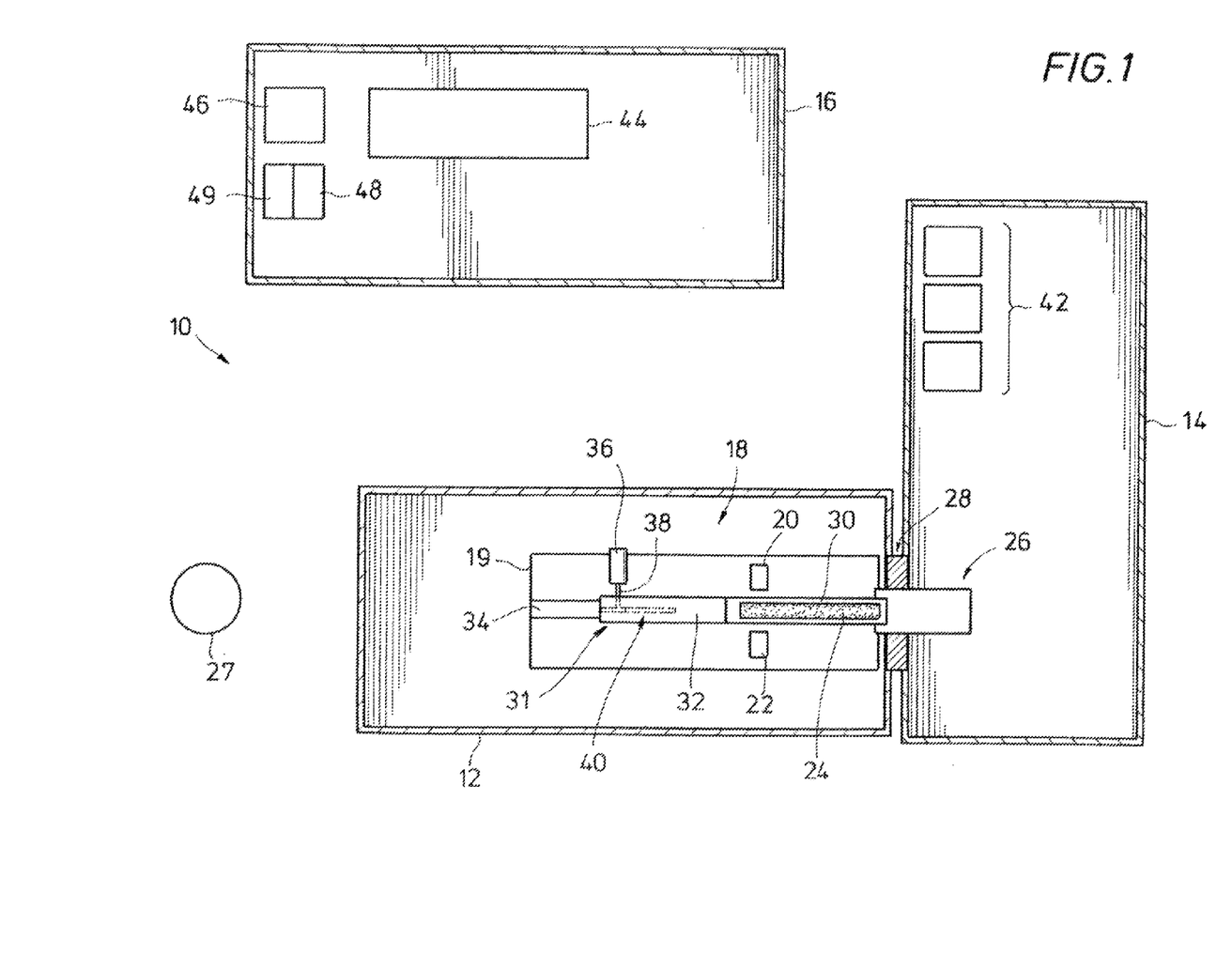
FIG. 1 is a plan partial sectional view of an example of a system for analyzing a core sample.

Shown in a plan partial sectional view in FIG. 1 is one example of a core analysis system 10, which includes first, second and third mobile enclosures. In the example of FIG. 1, the first mobile enclosure is a scan trailer 12, the second mobile enclosure is a handling trailer 14, and the third mobile enclosure is an analysis trailer 16. In one example, each of the enclosures may be part of a tractor trailer and which are movable by a tractor trailer. Schematically illustrated in the scan trailer 12 is a scan system 18, and substantially all of which is housed within a cabinet 19. In the illustrated example, cabinet 19 is specially designed to shield any radiation within, generated, inherent, or otherwise, from making its way to outside of the cabinet 19. Thus, cabinet 19 is in compliance with 21 C.F.R. 1020.40. Further shown in cabinet 19 is a scan source 20, which in one embodiment includes a device for emitting radiation, such as but not limited to an X-ray. A scan receiver 22 is also shown provided within cabinet 19 and combined with scan source 20, in one example, forms a computerized topography (CT) scanner.

An elongate and cylindrical core sample 24 is shown axially inserted within scan system 18. Core sample 24 is disposed into scan system 18 through a loading assembly 26, which is shown coupled to one end of the scan system 18 and projecting through an opening in a side wall of handling trailer 14. In an example, core sample 24 is taken from a subterranean formation below system 10, and is retrieved via a wellbore 27 shown adjacent system 10. Thus the wellbore 27 intersects the subterranean formation. Embodiments exist where the system 10 is "onsite" in the field and where the distance between the wellbore 27 to system 10 can range from less than one hundred yards up to five miles, and any distance between. Accordingly, real time analysis while drilling the wellbore 27 can take place within the system 10. Feedback from the analysis can be used by the drilling operator to make adjustments or changes to the drilling operation.

A hatch assembly 28 is schematically illustrated which provides the coupling interface between trailers 12, 14 and includes sealing around the loading assembly 26. While in scan system 18, core sample 24 rests on a core carrier 30. Core carrier 30 is part of a manipulator system 31, which further includes a manipulator arm 32 that telescopingly moves along a manipulator base 34. As shown, an end of manipulator arm 32 distal from manipulator base 34 couples onto an end of core carrier 30, so that core carrier is basically cantilevered on an end of the manipulator arm 32. Manipulator arm 32 is shown in an extended position over manipulator base 34. Manipulator arm 32 axially moves with respect to manipulator base 34 via a motor 36 shown having a shaft 38 that couples to manipulator arm 32. In one example, motor 36 is a linear direct current motor. A gear (not shown) on an end of shaft 38 distal from motor 36 engages a gear rack 40 that is provided on manipulator arm 32. Accordingly, selectively operating motor 36 urges manipulator arm 32, core carrier 30 and core sample 24 in an axial direction with respect to scan source 20. Moving manipulator arm 32 into a refracted position onto manipulator base 34 positions the entire length of core sample 24 in scan system 18, so that all of core sample 24 may be analyzed by the scan system 18. In one example, the scan source 20 and scan receiver 22 orbit around the core sample 24 and so that when in combination of axial movement of core sample 24 within system 18, a scan is taken of core sample 24. Further optionally, motor 36, or additional motors not shown, may manipulate and selectively move manipulator arm vertically and/or laterally to thereby better position core sample 24 into a designated orientation and/or spatial position during the scanning process.

Further shown in FIG. 1 are a series of work surfaces 42 provided within handling trailer 14. In one example of operation, before or after core sample 24 is scanned, it may be broken into sections for further analysis and analyzed on surfaces 42. Examples of the surfaces 42 include a crusher, sample divider, and mortar grinder. Additional analysis may take place within analysis trailer 16. Schematically illustrated within analysis trailer 16 is a nanotom 44, which can include a scanning system for scanning the internals of core sample 24, or parts of the core sample. Further shown in the analysis trailer 16 is a laser induced spectroscope 46, a Raman spectroscope 48, and near infrared spectroscope 49.

Figure 2:
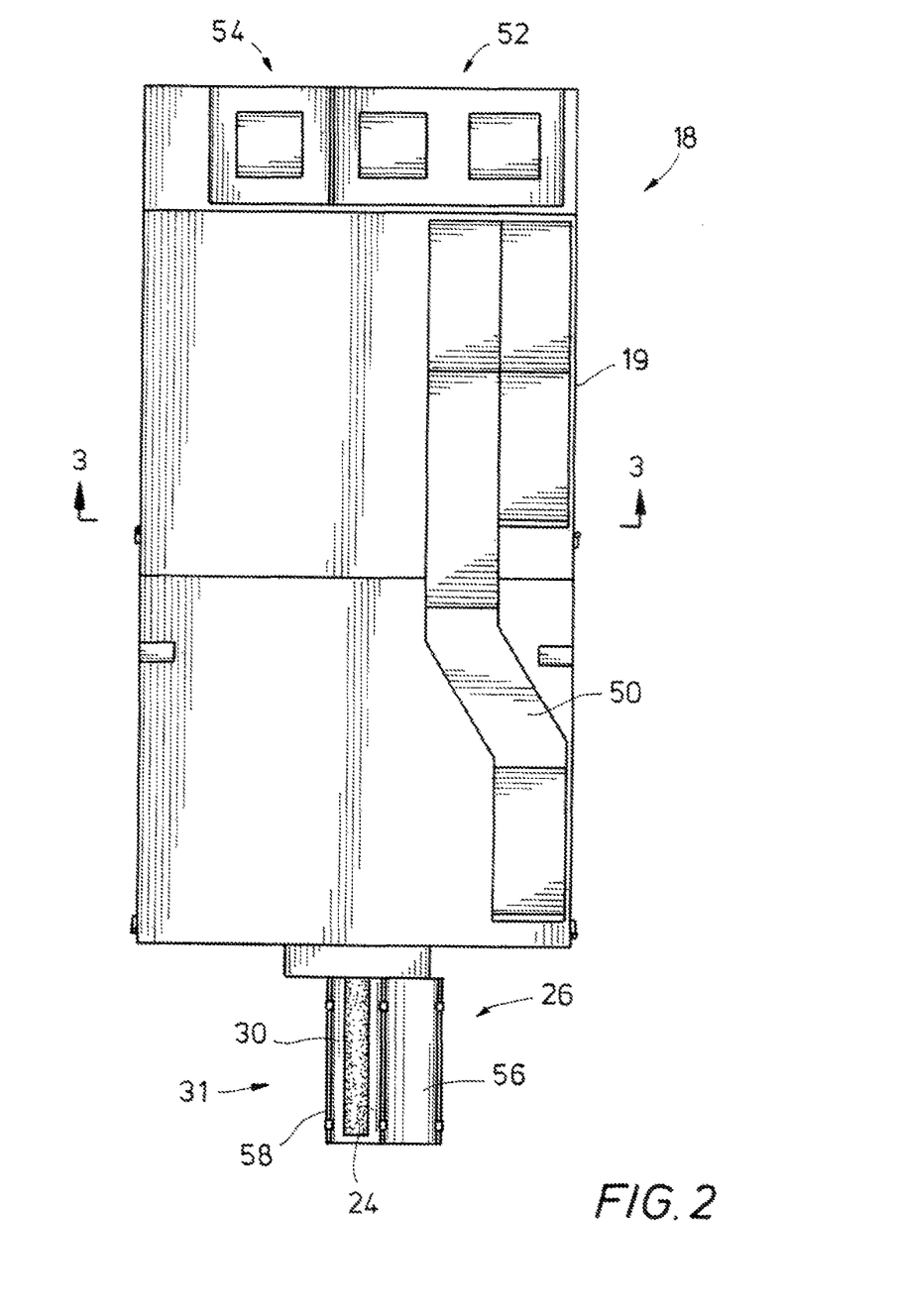
FIG. 2 is an overhead view of an example of a cabinet for housing a scanning unit for a core sample.

Referring now to FIG. 2, shown in an overhead view is an example of the scan system 18 and an upper surface of cabinet 19. Further illustrated in this example is a conditioning vent 50 on an upper end of the cabinet 19, where conditioning vent 50 provides a path for airflow and that is used in conditioning the inside of the cabinet 19. An advantage of the conditioning vent 50 is that conditioned air at proper temperature and humidity may be injected into the inside of cabinet 19 so that the sensitive device is housed within the cabinet 19 may be maintained in proper operating conditions to ensure normal operating functionality. A power distribution panel 52 is shown provided at an aft end of cabinet 19, and which includes buses (not shown) and other devices for distributing power through cabinet 19 into scan system 18. A control panel 54 is shown adjacent power distribution panel 52 and includes hardware and software for managing control of the operation of the systems house within cabinet 19. Projecting outward past the forward end of cabinet 19 is the loading assembly 26 in an open configuration. In the illustrated example, the loading assembly 26 includes a loading cover 56 and loading basin 58, where the loading cover 56 is shown swung open from a loading basin 58. As shown the core sample 24 has been inserted into open loading assembly 26 and onto the core carrier 30. As will be described in more detail below, safety features are included with the system that prevent operation of the manipulator system 31 when the loading assembly 26 is in the open position of FIG. 2.

Figure 3:
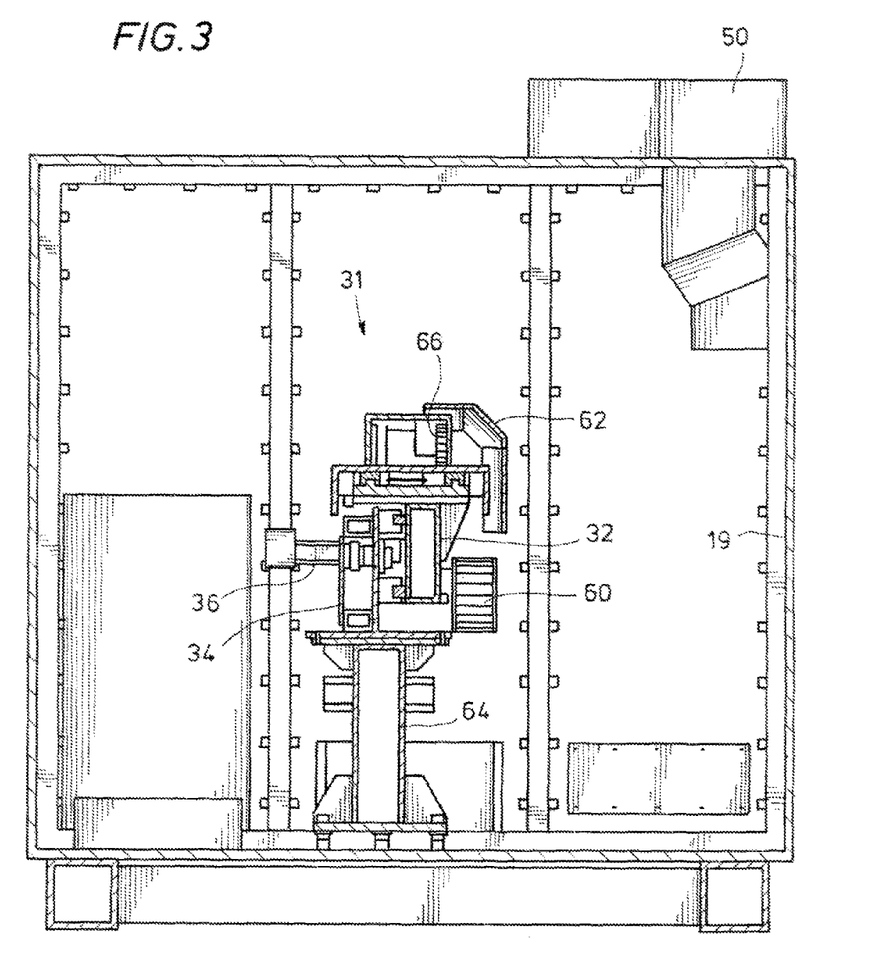
FIG. 3 is an axial sectional view of the cabinet of FIG. 2 and taken along lines 3-3.

FIG. 3 shows an example of the cabinet 19 in a sectional view and taken along lines 3-3 of FIG. 2. This view which is taken along the axial portion of manipulator system 31 shows one example of a wiring track 60; which has cross members for organizing the control and power wires needed for use in the scan system 18 and as the manipulator arm 32 axially moves with respect to manipulator base 34. Wiring track 60 maintains the wires in a designated location and position with use of wiring track 60 during operation of the manipulator system 31. Further in the example of FIG. 3 is a shroud 62 shown mounted on an upper end of manipulator system 31 and which covers a portion of the upper end and shields components within the manipulator system 31. Manipulator base 34 (and thus manipulator arm 32) is supported on a vertical mounting pedestal 64, which has a generally rectangular cross section along its axis, and has a lower end mounted on the floor of cabinet 19. Shown housed within shroud 62 is a wiring bus 66 which extends axially along the manipulator assembly.

Figure 4:
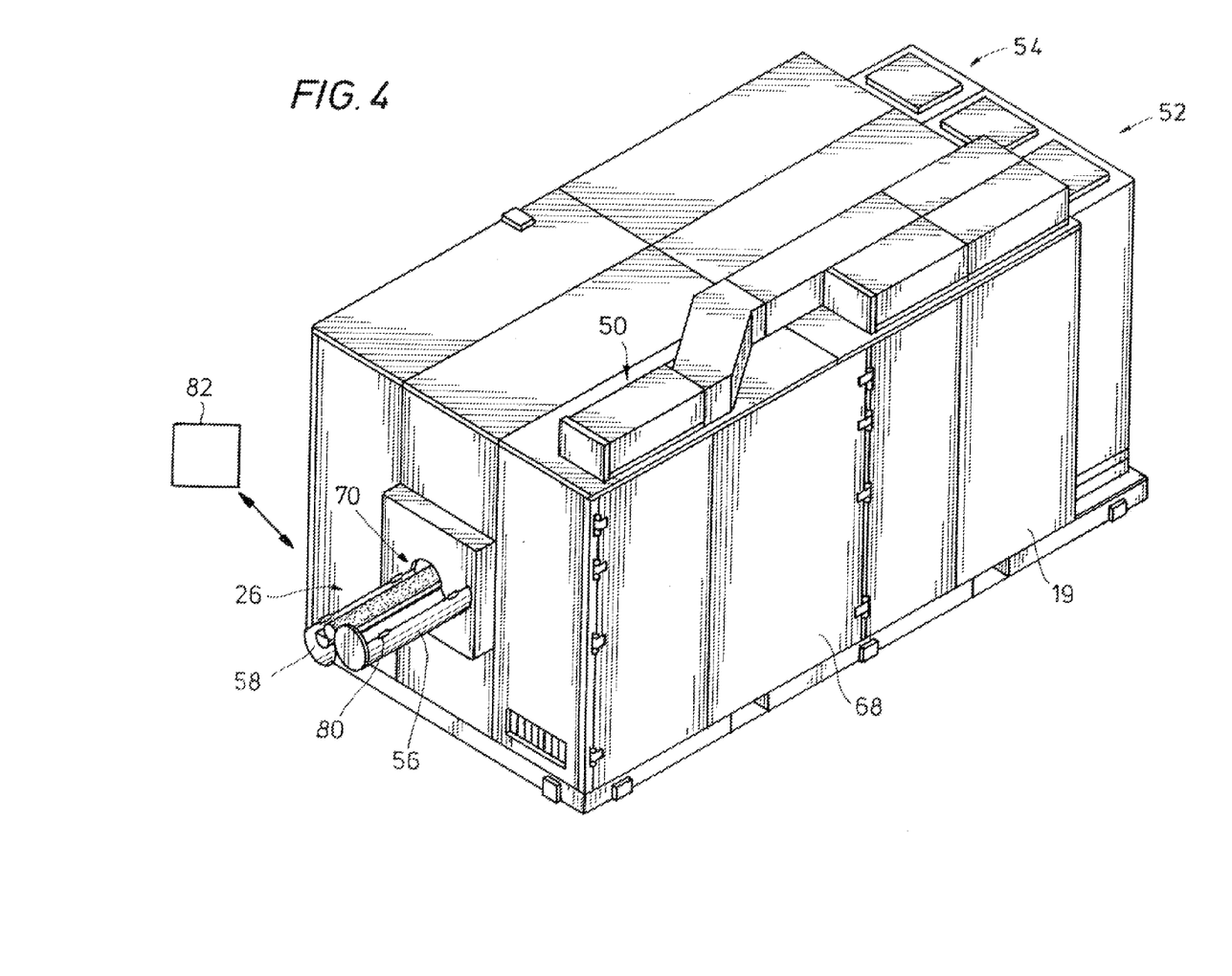
FIG. 4 is a perspective view of the cabinet of FIG. 2.
Figures 5, 6, 7A, 7B, 7C, 7D:
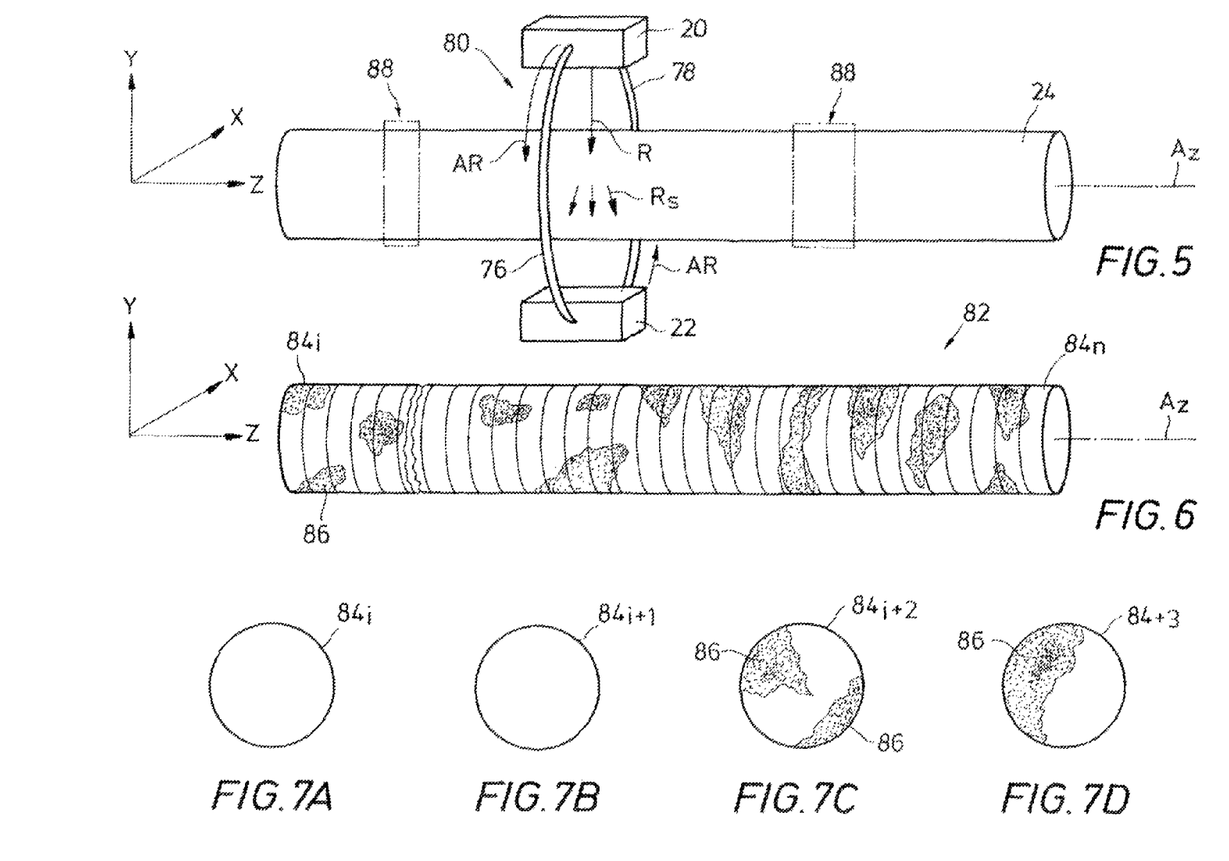
FIG. 5 is a perspective view of an example of scanning the core sample of FIG. 1.
FIG. 6 is an example of a composite image formed from the step of scanning of FIG. 5.
FIGS. 7A-7D are axial views of segments of the composite image of FIG. 6.

FIG. 4 provides in perspective view of one example of the cabinet 19 and having hinged panel 68 along its outer surface. As indicated above, the structure of cabinet 19 is in compliant with 21 C.F.R. 1020.40. Thus proper protective shielding is provided in the panel 68 and along the hinged interface. An additional safety feature is a door assembly 70 which includes a barrier (not shown) that slides axially across the opening shown at the base of the loading assembly 26 and in a forward wall of cabinet 19. The barrier thus provides a radiation shield from the inside to the outside of cabinet 19. An interlock connector 72 is shown provided on the loading cover 56 and loading basin 58. The interlock connectors 72 thus may recognize when the cover 56 is in the open position of FIG. 4 and in combination with controller 74 may prevent operation of the manipulator assembly. However, the control system associated with the scan system 18 that allows for motion of the manipulator assembly when the cover 56 is in the closed position and interlock connectors are adjacent one another Shown in FIG. 5 are curved supports 76, 78 that provide a mounting assembly for scan source 20 and scan receiver 22. The combination of support 76 and support 78 define a gantry system 80 that when rotated puts the scan source 20 and scan receiver 22 at an orbiting rotation around the core sample 24 and provides the scanning capabilities of the scan system 18. Curved arrows $A_R$ provide one example direction of rotation of the gantry system 80 for orbiting the scan source 20 and scan receiver 22 around the sample core 24. Further in this example, the manipulator system 31 (FIG. 1) selectively moves the core sample 24 bi-directionally along axis $A_Z$. As the gantry system 80 orbits the scan source 20 and scan receiver 18 around the axially moving core sample 24, radiation R is emitted from the scan source 20 into the core sample 24. Some of the radiation R scatters from the core sample 24 to create scattered radiation $R_S$, which can be received by the scan receiver 22.

The scan receiver 22 collects the radiation R and scattered radiation $R_S$ at multiple angular locations about axis $A_X$ of the core sample 24. In the example illustrated in FIG. 6, the data collected by the scan receiver 22 is used to create a composite image 82 that represents the core sample 24, and that also visually depicts physical characteristics of the core sample 24. The embodiment of the composite image 82 illustrated substantially replicates the form of the core sample 24 of FIG. 5. In an example, the composite image 82 is made up of voxels, where each voxel represents a volume of the core sample 24, and where each voxel has a characteristic or value that relates back to the volume of the core sample 24 it represents. Embodiments exist where the characteristic or value of the voxel represents a physical characteristic of the volume of the core sample 24 relating to the voxel. In the example of FIG. 6, the composite image 82 is made up of a series of disk like segments $84_1$-$84_n$ shown coaxially aligned along axis $A_{Zi}$. In an alternative, each of the segments $84_1$-$84_n$ is created by one orbit of the scan source 20 scan receiver 22 around the core sample 24. Alternatives exist wherein each of the segments $84_1$-$84_n$ represents about a 5 mm wide axial slice of the core sample 24. Portions 86 of the composite image 82 are shaded to reflect different physical characteristics in locations of the core sample 24 that spatially correspond to locations in the composite image 82. In an example, the image 82 is formed to emulate the core sample 24. Moreover, optional X-Y-Z axes are provided with both FIGS. 5 and 6 so that characteristics of a point or region in the core sample 24 can be identified in a point or region of the composite image 82 using corresponding X, Y, Z values, or range of values, from the X-Y-Z axes.

In an embodiment, the radiation absorption of the material making up the core sample 24 is estimated by the radiation received by the scan receiver 22. Portions 86 in the example composite image 82 are shaded based on the amount of radiation absorption estimated in corresponding locations in the core sample 24. For the purposes of simplicity, the composite image 82 is shown to have only shaded and non-shaded areas. However, the image 82 could have a multiplicity of colors to reflect how the core sample 24 has many different segments with varied characteristics. In an example operation, values of radiation absorption measured in discrete spaces in the core sample 24 are compared with radiation absorption values measured in other discrete spaces in the core sample 24. In one example step of determining which spaces to represent with shading is based on relative values of measured radiation absorption within the core sample 24 rather than comparing measured radiation absorption values with historical data. The step of determining what spaces or voxels to shade can alternatively involve estimating an average value of the radiation absorption measured in the spaces within the core sample 24, and then shading spaces or voxels in the composite image 82 depending on the value of the radiation absorption in the corresponding space in the core sample 24. For example, shading can be assigned if the radiation absorption value is above or below the average radiation absorption value, or if the specific radiation absorption value of the space in the core sample 24 is offset a threshold percentage or deviation from the average radiation absorption value. In one alternate embodiment, radiation attenuation of the core sample 24 is measured, which can be one or a combination of radiation absorption, radiation transmission, and radiation scattering.

FIGS. 7A-7D are axial views of side surfaces of a series of adjacent segments $84_i$-$84_{i+3}$ where the shape and location of the portions 86 of different characteristics may vary between the adjacent segments $84_i$-$84_{i+3}$. As shown in FIGS. 7A and 7B, the example segments $84_i$, $84_{i+1}$ are substantially non-shaded. As such, it can be deduced that the portions of the core sample 24 represented by segments $84_i$-$84_{i+1}$ are substantially homogenous without changes in their material properties. In contrast, segments $84_{i+2}$ and $84_{i+3}$ have portions 86 that are shaded, and where the portions 86 in those adjacent segments $84_{i+2}$ and $84_{i+3}$ have different shapes and locations. In an example it is estimated that the material characteristics changes in the portions of the core sample 24 represented by segments $84_{i+2}$ and $84_{i+3}$. In an example embodiment, zones of interest 88 (FIG. 5) are identified based on where material characteristics of the core sample 24 are estimated to be changing based on scan data as described above. Optionally, a change in an average value reflected within voxels or other values assigned to locations in a specific segment 84 can identify the presence of a zone of interest 88. In yet another alternative, a zone of interest 88 is identified when particular values represented in a specific segment 84 are outside of a designated range, or when particular values represented in a specific segment 84 exceed a designated spread.

Identifying the zones of interest 88 from the scan process described above, and from correlating the spatial reference coordinate systems (i.e. X-Y-Z axes), can pinpoint what portions of the core sample 24 to analyze with further detail. For example, plugs can be extracted from the zone of interest 88 of the core sample 24 for additional analysis, such as in the nanotom 44 or by spectroscopy as described in relation to FIG. 1 above. An example plug can have a cylindrical shape with a diameter and or length that ranges in the centimeters, and is therefore substantially smaller than core sample 24, which can have a length that exceeds one meter. Alternatively, embodiments of plugs can have any shape and any size, which can be obtained by slicing, scraping, granulating and the like. A significant advantage exists by focusing plug extraction to the zone of interest 88 rather than random locations on the core sample 24, as more information can be obtained from plugs taken from zone(s) of interest 88 in the core sample 24 over those taken from locations in the core sample 24 with characteristics that are substantially homogeneous. As plug preparation can be time consuming, an additional advantage is realized in the time savings gained by a focused approach of obtaining a few plugs in the zone(s) of interest 88 instead of many plugs over the entire core sample 24.

In examples where constituents throughout the core sample 24 have physical characteristics with a range of multiplicity of values, sections in the composite image 82 that represent the core sample 24 can be assigned alphanumeric values that correlate to those physical characteristics. Examples of the physical characteristics include homogeneity, density, average density, and median density of the material in the core sample 24.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. In an example embodiment, the zone of interest 88 is strategically chosen so that the formation adjacent wellbore 27 can be represented by analyzing the zone of interest 88. In another embodiment, clays, minerals, and other elements in the zone of interest 88 are identified. These and other similar modifications will readily suggest themselves to those skilled in the art, and are intended to be encompassed within the spirit of the present invention disclosed herein and the scope of the appended claims.

What is claimed is:

1. A method of analyzing a core sample comprising:
   scanning the core sample with radiation, the radiation originating from a scan source arranged proximate the core sample;
   forming a composite image of the core sample, the composite image being indicative of one or more characteristics of the core sample and illustrating an amount of radiation attenuated by one or more portions of the core sample, the composite image spatially correlating to a position along the core sample;
   comparing the one or more portions of the core sample with other portions of the core sample along an axis of the core sample based at least in part on the respective composite images of the one or more portions;
   identifying a zone of interest in the core sample based on the comparison, the zone of interest based on the amount of radiation attenuated by the one or more portions of the core sample; and
   analyzing the zone of interest in the core sample based at least in part on the composite image representing the one or more characteristics of the core sample to strategically represent a formation adjacent a wellbore.

2. The method of claim 1, wherein the step of obtaining information about characteristics of the core sample comprises scanning the core sample with radiation, monitoring radiation scattered from the core sample, and estimating an amount of radiation absorbed in volumetric spaces of the core sample.

3. The method of claim 1, further comprising forming the composite image of the core sample that spatially represents characteristics of the core sample.

4. The method of claim 3, wherein the composite image comprises voxels that are strategically located to represent corresponding volumetric spaces of the core sample.

5. The method of claim 4, wherein the voxels are assigned a designated value to represent the corresponding characteristics of the volumetric space of the core sample.

6. The method of claim 4, wherein the designated value comprises an alpha-numeric attribute.

7. The method of claim 3, wherein the composite image comprises segments that are coaxially arranged and that represent axial slices of the core sample, and wherein the step of identifying a zone of interest comprises identifying changes in characteristics of the core sample represented by multiple segments.

8. The method of claim 7, wherein the multiple segments are adjacent one another.

9. The method of claim 1, wherein the step of comparing the one or more portions of the core sample comprises estimating an average value the characteristics of the core sample.

10. The method of claim 1, wherein the zone of interest in the core sample is identified where there is a change of the one or more characteristics of the core sample.

11. The method of claim 1, wherein the step of analyzing the zone of interest in the core sample comprises obtaining a plug from the core sample and scanning the plug with an amount of radiation that exceeds an amount of radiation that scanned the sample plug.

12. A method of analyzing a core sample comprising:
    measuring a value of radiation attenuation at discrete volumetric spaces in the core sample;
    generating a composite image of the core sample, the composite image illustrating the radiation attenuation at the discrete volumetric spaces, the composite image spatially correlating to a position along the core sample;
    estimating a physical characteristic of the core sample at each of the discrete volumetric spaces based on a measured radiation attenuation;
    identifying differences between physical characteristics of proximate discrete volumetric spaces based at least in part on the composite image;
    designating a zone of interest in the core sample to be where the differences between physical characteristics of proximate discrete volumetric spaces exceed a threshold value; and
    analyzing the zone of interest in the core sample based at least in part on the composite image representing the radiation attenuation to strategically represent a formation adjacent a wellbore.

13. The method of claim 12, further comprising creating voxels that are assigned a location that correlates to the discrete volumetric spaces and are assigned a value that represents the physical characteristics of the corresponding discrete volumetric spaces.

14. The method of claim 13, further comprising forming the composite image based on the voxels.

15. The method of claim 12, further comprising obtaining plugs from the zone of interest.

16. The method of claim 15, further comprising scanning the plugs with a computerized tomography scan.

17. The method of claim 15, further comprising performing spectroscopy on the plug.

18. The method of claim 12, further comprising designating a multiplicity of zones of interest in the core sample and analyzing the zones of interest.

19. The method of claim 12, wherein radiation attenuation comprises radiation absorption.

\* \* \* \* \*